United States Patent [19]

Cosand et al.

[11] Patent Number: 5,075,211

[45] Date of Patent: Dec. 24, 1991

[54] SYNTHETIC ANTIGEN FOR THE DETECTION OF AIDS-RELATED DISEASE

[75] Inventors: Wesley L. Cosand, Bothell; Linda J. Harris, Seattle; Raymond L. Houghton, Kirkland, all of Wash.

[73] Assignee: Genetic Systems Corporation, Redmond, Wash.

[21] Appl. No.: 930,785

[22] Filed: Nov. 14, 1986

Related U.S. Application Data

[63] Continuation-in-part of Ser. No. 844,485, Mar. 26, 1986, which is a continuation-in-part of Ser. No. 767,303, Aug. 19, 1985, Pat. No. 4,629,783, which is a continuation-in-part of Ser. No. 728,052, Apr. 29, 1985, abandoned.

[51] Int. Cl.[5] ...................... G01N 33/569; C07K 7/10

[52] U.S. Cl. ........................................ 435/5; 435/7.9; 435/7.92; 435/974; 530/324; 530/826; 930/221; 930/DIG. 821

[58] Field of Search ...................... 435/5, 7, 7.92, 7.9, 435/974, 826; 530/324, 826; 930/221, 821

[56] References Cited

U.S. PATENT DOCUMENTS

| | | | |
|---|---|---|---|
| 4,629,783 | 12/1986 | Cosand | 530/324 |
| 4,661,445 | 4/1987 | Saxinger et al. | 435/7 |
| 4,704,357 | 11/1987 | Mitsuya et al. | 435/32 |
| 4,708,818 | 11/1987 | Montagnier et al. | 435/5 |
| 4,716,102 | 12/1987 | Levy | 435/5 |
| 4,833,072 | 5/1989 | Krchnak et al. | |

FOREIGN PATENT DOCUMENTS

| | | |
|---|---|---|
| 0181150 | 5/1986 | European Pat. Off. |

OTHER PUBLICATIONS

Chanh et al., "Induction of anti-HIV neutralizing antibodies by synthetic peptides" EMBO Journal, 5(11) 3065-3071, 1986.

Steimer et al., "Recombinant Polypeptide from the Endonuclease Region of the Acquired Immune Deficiency Syndrome Retrovirus Polymerase (pol) Gene Detects Serum Antibodies in Most Infected Individuals" Journal of Virology, 5B(1) 9-16, 1986.

Kennedy et al., "Antiserum to a Synthetic Peptide Recognizes the HTLV-III Envelope Glycoprotein" Science, 231 1556-59, 3/28/86.

Chanh et al., "Human immunodeficiency virus gp120 glycoprotein detected by a monoclonal antibody to a synthetic peptide" Eur. J. Immunology 16: 1465-1468 (1986).

Arya et al., "Three novel genes of human T-lymphotropic virus type III: Immune reactivity of their products with sera from acquired immune deficiency syndrome patients" Proc. Natl. Acad. Sci. USA, 83: 2209-2212 Apr. 1988.

Allan et al., "Major Glycoprotein Antigens That Induce Antibodies in AIDS Patients are Encoded by HTLV-III" Science 228:1091-1094, 5/31/85.

Crowl et al., "HTLV-III env Gene Products Synthesized in *E. coli* Are Recognized by Antibodies Present in the Sera of AIDS Patients" Cell 41:979-986, Jul., 1985.

Ortho Diagnostic Systems, "Synthetic peptides for human T cell leukemia virus test", Chemical Abstracts 105 (1986) abstract #173060j.

Wang et al., "Detection of antibodies to human T-lymphotropic virus type III by using a synthetic peptide of 21 amino acid residues corresponding to a highly antigenic segment of gp41 envelope protein", Proc. Natl. Acad. Sci. USA 83:6159-6163, Aug. 1986.

*Primary Examiner*—Christine Nucker

*Attorney, Agent, or Firm*—Townsend and Townsend

[57] ABSTRACT

Novel peptides are provided having substantially the same sequence as immunologically significant fragments of AIDS-related viruses. The polypeptides can be used as reagents in the determination of exposure of a human host to the virus. Of particular interest is the use of polypeptides in screening blood products.

23 Claims, No Drawings

SYNTHETIC ANTIGEN FOR THE DETECTION OF AIDS-RELATED DISEASE

This application is a continuation-in-part of U.S. application Ser. No. 844,485, filed Mar. 26, 1986, which is a continuation-in-part of U.S. application Ser. No. 767,303, filed Aug. 19, 1985, now U.S. Pat. No. 4,629,783, which is a continuation-in-part of U.S. application Ser. No. 728,052, filed Apr. 29, 1985, now abandoned.

BACKGROUND OF THE INVENTION

1. Field of the Invention

With the discovery that the diseases called lymphadenopathy syndrome and acquired immune deficiency disease (AIDS) are caused by an infectious retrovirus designated lymphadenopathy virus (LAV), human T-cell lymphotropic virus-III (HTLV-III), AIDS-related virus (ARV), or immune deficiency-associated virus (IDAV), there has become an immediate need to be able to detect potential vectors of the disease, such as blood from diseased individuals, which may be employed for transfusions or from which specific blood factors may be isolated.

To detect potential vectors of the disease, it is necessary to have viral proteins and/or antibodies to such proteins. Because of the hazards associated with growing the LAV/HTLV-III retrovirus, ther eis significant interest in establishing means for obtaining the viral proteins or their immunlogic equivalents, which means do not necessitate handling large volumes of live, potentially infectious virus. In choosing alternatives, one must be concerned with the fact that the viruses have been reported to be highly polymorphic, frequently changing as the retrovirus is passaged.

2. Brief Description of the Relevant Literature

The various antigens of the retrovirus are described by Saxinger et al., *Science* (1985) 227:1036–1038. See also Gall et al., ibid. (1984) 224:500; Sarangadharn et al., ibid. 224:506; Barre-Sinoussi et al., ibid. (1983) 220:868; Montagnier et al., in *Human T-Cell Leukemia/Lymphoma Virus*, Gallo, Essex, Gross, eds. (Cold Spring Harbor Laboratory, Cold Spring Harbor, N.Y.), 1984, p. 363. These may include, but are not limited to, p13, p18, p25, p36, gp43, p55, gp65, gp110, etc., where the numbers may differ depending upon the reporter.

Hopp and Woods, *Proc. Natl. Acad. Sci. USA* (1981) 78:3824, describe criteria for selecting peptides as potential epitopes of polypeptides based on their relative hydrophilicity. In one study employing these criteria, a 12-amino acid peptide was synthesized that bound 9% of antibodies elicited by the native protein (Hopp, *Molec. Immunol.* (1981) 18:869). In general, Hopp/Woods critera have been shown not to have a high predictive value. Furthermore, epitopes have been demonstrated which are not hydrophilic (Kazim et al., *Biochem. J.* (1982) 203:201). Other studies of polypeptide antigenicity include Green et al., *Cell* (1982) 28:477, where peptides were employed which elicited antibodies, which antibodies were capable of binding to the native protein, while conversely antibodies which were elicited by the native protein failed to bind to the peptides, and Trainer et al., *Nature* (1984) 312:127, whose results with myohaemerythrin paralleled those of Green et al.

The complete nucleotide sequence of LAV is reported by Wain-Hobson et al., *Cell* (1985) 40:9. The complete sequence for HTLV-III is reported by Meusing et al., *Nature* (1985) 313:450, while the complete sequence for ARV is reported by Sanchez-Pescador et al., *Science* (1985) 227:484. All three viruses exhibit substantial nucleotide homology and are similar with rsepect to morphology, cytopathology, requirements for optimum reverse transcriptase activity, and at least some antigenic properties (Levy et al., *Science* (1984) 225:840; Shupbach et al., *Science* (1984) 224:503), and hence should be considered isolates of the same virus. See also, Chang et al., *Sicence* (1985) 228:93. Based on these and other data the Human Retrovirus Subcommittee of the International Committee on the Taxonomy of Viruses has proposed the name Human Immuno-deficiency Virus (HIV) for this group of closely related viruses (*Science* (1986) 232:697). This designation will be used within this application.

SUMMARY OF THE INVENTION

Peptide sequences capable of immunologically mimicking proteins encoded in the pol and gag regions of the HIV retrovirus are provided as reagents for use in the screening of blood and blood products for prior exposure to the retrovirus. The peptides are at least 5 amino acids in length and can be used in various specific binding assays for the detection of antibodies to HIV virus, for the detection of HIV antigens, or as immunogens.

DESCRIPTION OF THE SPECIFIC EMBODIMENTS

For the purpose of this disclosure, a virus is considered to be the same as or equivalent to HIV if it substantially fulfills the following criteria:

(a) The virus is tropic for T-lymphocytes, especially T-helper cells ($CD4^+$, according to the international nomenclature defined in Bernard et al., eds. *Leucocyte Typing*, New York: Springer Verlag, 1984).

(b) The virus is cytopathic for infected $CD4^+$ cells (rather than transforming, as are HTLV-I and -II);

(c) The virus encodes an RNA-dependent DNA polymerase (reverse transcriptase) which is $Mg^{2+}$-dependent (optimum concentration 5 mM), has a pH optimum pf 7.8, is not inhibitable by actinomycin D, and can employ oligo$(dT)_{12\text{-}18}$ as a primar for reverse transcription from its 3' LTR;

(d) The virus bands in a sucrose gradient at a density of approximately 1.16;

(e) The virus can be labeled with $[^3H]$-uridine;

(f) The virus is substantially cross-reactive immunologically with the proteins encoded by the gag, env, and pol regions of HIV; and (g) The virus shares substantial nucleotide homology (approximately 75–100%) with LAV or HTLV-III.

Novel peptides are provided which immunologically mimic proteins encoded by the HIV retrovirus, particularly proteins encoded by the pol region of the viral genome. To accommodate strain-to-strain variations among different isolates, adjustments for conservative substitutions, and selection among the alternatives where non-conservative substitutions are involved, may be made. These peptides can be used individually or together for detection of the virus or of antibodies to the virus in a physiological sample. Depending upon the nature of the test protocol, the peptides may be labled or unlabeled, bound to a solid surface, conjugated to a carrier or other compounds, or the like.

The peptides of interest will be derived from the peptides encoded by the pol and gag regions. These peptides will be primarily derived from p31 of the pol region and from p25 of the gag region. These peptides will be given Roman numerals and will also be given numerical designations, which are arbitrarily associated with the manner in which they were produced, in this application. Of particular interest is the coding region extending from about base pair (bp) 4265 to bp 4519, particularly from about bp 4265 to bp 4399 and from bp 4385 to bp 4519, including a shorter segment from bp 4430 to bp 4519. Also, the coding region extending from about bp 897 to bp 986 is of particular interest. (Numbering according to Wain-Hobson et al., supra.)

The peptides of interest will include at least 5, sometimes 6, sometimes 8, sometimes 12, usually fewer than about 50, more usually fewer than about 35, and preferably fewer than about 25 amino acids included within a sequence coded for by the HIV retrovirus. In each instance, desirably the oligopeptide will be as small as possible while still maintaining substantially all of the sensitivity of the larger peptide. In some instances it may be desirable to join two or more oligopeptides which are non-overlapping to form a single peptide structure or to use them as individual peptides at the same time, which separately or together provide equivalent sensitivity to the parent.

The peptides may be modified by introducing conservative or non-conservative substitutions in he peptides, usually fewer than 20 number percent, more usually fewer than 10 number percent of the amino acids being exchanged. In those situations where regions are found to be polymorphic, it may be desirable to vary one or more particular amino acids to more effectively mimic the differing epitopes of the different retroviral strains.

It should be understood that the polypeptides employed in the subject invention need not be identical to any particular HIV polypeptide sequence, so long as the subject compounds are able to provide for immunological competition with proteins of at least one of the strains of the HIV retrovirus. Therefore, the subject polypeptides may be subject to various changes, such as insertions, deletions, and substitutions, either conservative or non-conservative, where such changes might provide for certain advantages in their use. By conservative substitutions is intended substitutions within groups such as gly, ala; val, ile, leu; asp, glu; asn, gln; ser, thr; lys, arg; phe, tyr; and norleu, met. Usually, the sequence will not differ by more than 20% from the sequence of at least one strain of an HIV retrovirus except where additional amino acids may be added at either terminus for the purpose of providing an "arm" by which the peptides of this invention may be conveniently immobilized. The arms will usually be at least 1 amino acid and may be 50 or more amino acids, more often 1 to 10 amino acids, in length.

In addition, one or two amino acids may be added to the termini of an oligopeptide or peptide to provide for ease of linking of peptides one to another, for coupling to a support or larger peptide, for reasons to be discussed subsequently, for modifying the physical or chemical properties of the peptide or oligopeptide, or the like.

Amino acids such as tyrosine, cysteine, lysine, glutamic or aspartic acid, or the like may be introduced at the C- or N-terminus of the peptide or oligopeptide to provide for a useful functionality for linking. Cysteine is particularly preferred to facilitate covalent coupling to other peptides or to form polymers by oxidation. Combinations of cysteine with intervening amino acid spacers are also useful. For example, two cysteine residues can be separated by one or more α-amino acid residues having a single side chain containing no more than four carbon atoms (small size being desired to avoid interference with coupling reactions). Glycine residues are preferred for this reason, particularly one to three glycine residues between amino acids added to facilitate coupling. Cysteine residues are particularly useful in forming network polymers by oxidation. In such cases it is preferred to have at least three cysteine residues present in the molecules being linked, preferably by utilizing cysteine residues added to the terminal portions of the peptides.

In addition, the peptide or oligopeptide sequences may differ from the natural sequence by the sequence being modified by terminal-$NH_2$ acylation, e.g., acetylation, or thioglycolic acid amidation, terminal-carboxy amidation, e.g., with ammonia or methylamine, to provide sites for linking to a support or other molecule.

The peptides and oligopeptides of interest will now be considered. Peptide I (126) encoded in the region bp 4265 to bp 4399 will have the following amino acid sequence, where oligopeptides included within the following sequence will include linear epitopes within such sequence:

(I) (126)

Y—Gln—Val—Arg—Asp—Gln—Ala—Glu—His—Leu—

—Lys—Thr—Ala—Val—Gln—Met—Ala—Val—Phe—Ile—

—His—Asn—Phe—Lys—Arg—Lys—Gly—Gly—Ile—Gly—

—Gly—Tyr—Ser—Ala—Gly—Glu—Arg—Ile—Val—Asp—

—Ile—Ile—Ala—Thr—Asp—Ile—X—Z wherein X and Y are optionally present and when present represent amino acids that facilitate covalent coupling of the peptide to a protein carrier or other peptide or polymerization through an added cystein residue by oxidation. Z indicates that the carboxy terminal amino acid is present as either a free carboxy or as an amide. When X and Y independently represent one or more cysteine or a combination of one or more cysteine with spacer amino acids. Preferred spacer amino acids are α-amino acid residues having a single side chain containing no more than four carbon atoms. Glycine is a particularly preferred spacer. Preferred peptides for use in oxidative polymerization are those in which X and Y together represent at least three cysteine residues. When two cysteine residues are present at the same end of the peptide, a preferred embodiment exists when the cysteine residues are separated by from one to three spacer amino acid residues, preferably glycine.

Preferably, this peptide will have no more than about 45 amino acids encoded by the HIV genome.

The next peptide II (123) will be encoded by the region xtending from about bp 4385 to bp 4519 and will have the following sequence, where oligopeptides incldued within the following sequence will include linear epitopes within such sequence:

(II) (123)

Y—Ile—Ala—Thr—Asp—Ile—Gln—Thr—Lys—Glu—Leu—

—Gln—Lys—Gln—Ile—Thr—Lys—Ile—Gln—Asn—Phe—

—Arg—Val—Tyr—Tyr—Arg—Asp—Ser—Arg—Asp—Pro—

-continued

—Leu—Trp—Lys—Gly—Pro—Ala—Lys—Leu—Leu—Trp—

—Lys—Gly—Glu—Gly—Ala—X—Z wherein the amino terminal Y and the carboxy terminal X-Z have been defined previously.

Also of interest is the oligopeptide IIa:

(IIa) (124)

Y—Lys—Ile—Gln—Asn—Phe—Arg—Val—Tyr—Tyr—Arg—

—Asp—Ser—Arg—Asp—Pro—Leu—Trp—Lys—Gly—Pro—

—Ala—Lys—Leu—Leu—Trp—Lys—Gly—Glu—Gly—Ala—

—X—Z wherein X, Y and Z have been defined previously.

For the gag region peptide III (158) will be encoded by the region extending from about bp 897 to bp 986 and will have the following sequence, where oligopeptides included within the following sequence will include linear epitopes within such sequence:

(III) (158)

Y—Leu—Asn—Thr—Val—Gly—Gly—His—Gln—Ala—Ala—

—Met—Gln—Met—Leu—Lys—Glu—Thr—Ile—Asn—Glu—

—Glu—Ala—Ala—Glu—Trp—Asp—Arg—Val—His—Pro—

—X—Z wherein X, Y, and Z have been defined previously.

Of particular interest is the use of the mercaptan group of cysteins or thioglycolic acids used for acylating terminal amino groups or the like for linking two of the peptides or oligopeptides or combinations thereof by a disulfide linkage or a longer linkage. To achieve this, compounds may be employed having bis-haloacetyl groups, nitroarylhalides, or the like, where the reagents are specific for thio groups. Thus, the linking between the two mercapto groups of the different peptides or oligopeptides may be a single bond or a linking grou of at least 2, usually at least 4, and not more than about 16, usually not more than about 14 carbon atoms.

The subject peptides may be employed linked to a soluble macromolecular (e.g., ≳5 kDal) carrier. Conveniently, the carrier may be a poly(amio acid), either naturally occurring or synthetic, to which antibodes are unlikely to be encountered in human serum. Illustrative polypeptides include poly-L-lysine, bovine serum albumin, keyhole limpet hemocyanin, bovine gamma globulin, etc. The choice is primarily one of convenience and availability.

With such conjugates, there will be at least one molecule of at least one subject peptide per macromolecule and not more than about 1 per 0.5 kDal, usually not more than about 1 per 2 kDal of the macromolecule. One or more different peptides may be linked to the same macromolecule.

The manner of linking is conventional, employing such reagents as p-maleimidobenzoic acid, p-methyldithiobenzoic acid, maleic acid anhydride, succinic acid anhydride, glutaraldehyde, etc. The linkage may occur at the N-terminus, C-terminus or at a site intermediate to the ends of the molecule. The subject peptide mayb e derivatized by linking, may be linked while bound to a support, or the like.

The compounds may be employed as labeled or unlabeled compounds depending upon their use. (By label is intended a molecule which provides, directly or indirectly, a detectable signal.) Various labels may be employed, such as radionuclides, enzymes, cluorescers, chemiluminescers, enzyme substrates, cofactors or inhibitors, particles, e.g., magnetic particles, combinations of ligands and receptors, e.g., biotin and avidin, or the like. In addition, the polypeptides may be modified in a variety of ways for binding to a surface, e.g., microtiter plate, glass beads, chromatographic surface, e.g., paper, cellulose, silica gel, or the like. The particular manner in which the polypeptides are joined to another compound or surface is conventional and finds ample illustration in the literature. See, for example, U.S. Pat. Nos. 4,371,515; 4,487,715; and patents cited therein.

Various assay protocols may be employed for detecting the presence of either antibodies to retroviral proteins orretroviral proteins themselves. Of particular interest is using the peptide as the labeled reagent, where the label allows for a detectable signal, or binding the peptide, either directly or indirectly to a surface, where antibody to the peptide in the sample will become bound to the peptide on the surface. The presence of human antibody bound to the peptide can then be detected by employing a xenogeneic antibody specific for human immunoglobulin, normally both human IgM and IgG, or a labeled protein specific for immune complexes, e.g., Rf factor or *S. aureus* protein A.

Various heterogeneous protocols may be employed, either competitive or non-competitive. Peptide may be bound to a surface or support ("support") and labeled antibody allowed to compete with antibody in the sample of the limited amount of bound peptide. The amount of label bound to the support would be related to the amount of competitive antibody in the sample.

Antibody could be bound to the support and the sample combined with labeled peptide. After contact of the reaction mixture with the bound antibody, the amount of label bound to the support would relate to the amount of cognate antibody in the sample.

Xenogeneic anti-human antibody, e.g., antibodies to the $F_c$ of IgG and IgM (immunoglobulins), could be bound to a support. The sample would be contacted with the immunoglobulins and labeled peptide, whereby the amount of labeled peptide bound to the support would be indicative of the presence of the cognate antibodies.

Alternatively, homogeneous assays can be employed where the peptide is bound to an enzyme, fluorescer, or other lable, where the binding of antibody to the peptide results in being able to discriminate between the label involved with a specific binding pair complex and label which is not involved in the complex. For assays involving such techniques, see for example U.S. Pat. Nos. 3,817,837; 3,850,752; 3,901,654; 3,935,074; 3,984,533; 3,996,345; 4,034,074; and 4,098,876, whose disclosures are incorporated herein by reference.

As an illustration of the subject invention the subject peptides may be conjugated to a fluorescent molecule, such as fluorescein, rhodamine or umbelliferone. Various techniques may be used for detecting complex formation with antibodies, e.g., fluorescence polarization. In this assay the fluorescence polarization is different between complexed and uncomplexed peptide conjugate. Apparatuses are available for measuring changes in fluorescence polarization, e.g., TDx supplied by Abbott Laboratories, Chicago, Ill.

Illustrative of an assay technique is the use of sample container, e.g., microtiter-plate wells, where the subject polypeptides or conjugates thereof are adhered to the container bottom and/or walls either covalently or non-covalently. The sample, normally human blood or serum diluted in an appropriately buffered medium, is added to the container and a sufficient time allowed for complex formation between the polypeptide(s) and any cognate antibodies int he sample. The supernatant is removed and the container washed to remove non-specifically bound proteins.

A labeled specific binding protein which specifically binds to the complex is employed for detection. To the container may be added xenogeneic antisera to human immunoglobulin, particularly anti-(human IgM and IgG) in an appropriately buffered medium. The xenogeneic antisera will normally be labeled with a detectable lable, e.g., radionuclide or enzyme. Instead of antisera, proteins specific for the immune complex may be employed, e.g., *S. Aureus* protein A. The label may then be detected. For example, with an enzyme, after removal of non-specifically bound enzyme label, a developer solution is added. The developer solution will contain an enzyme substrate and possibly enzyme cofactors, chromogens, etc., which, upon reaction, provide a colored or fluorescent product which may be detected colorimetrically or fluorimetrically, respectively.

The peptides can be prepared in a wide variety of ways. The peptides, because of their relatively short size, may be synthesized in solution or on a solid support in accordance with conventional techniques. Various automatic synthesizers are commercially available today and can be used in accordance with known protocols. See, for example, Stewart and Young, Solid Phase Peptide Synthesis, 2nd ed., Pierce Chemical Co., 1984; and Tam et al., *J. Am. Chem. Soc.* (1093) 105:6442.

Alternatively, hybrid DNA technology may be employed where a synthetic gene may be prepared by employing single strands which code for the polypeptide or substantially complementary strands thereof, where the single strands overlap and can be brought together in an annealing medium so as to hybridize. The hybridized strands may then be ligated to form the complete gene, and, by choice of appropriate termini, the gene may be inserted into expression vectors, which are readily available today. See, for example, Maniatis et al., Molecular Cloning, A Laboratory Manul, CSH, Cold Spring Harbor Laboratory, 1982. Or, the region of the viral genome coding for the peptide may be cloned by conventional recombinant DNA techniques and expressed (see Maniatis, supra).

DNA coding sequences which may be used for expressing the peptides include the following:

(TGT GGA GGA TGT) CAG GTA AGA GAT CAG I
GCT GAA CAT CTT AAG ACA GCA GTA CAA ATG GCA
GTA TTC ATC CAC AAT TTT AAA AGA AAA GGG GGG
ATT GGG GGG TAC AGT GCA GGG GAA AGA ATA
GTA GAC ATA ATA GCA ACA GAC ATA (TGT);

(TGT GGA GGA TGT) ATA GCA ACA GAC ATA II
CAA ACT AAA GAA TTA CAA AAA CAA ATT ACA AAA
ATT CAA AAT TTT CGG GTT TAT TAC AGG GAC AGC

-continued

AGA GAT CCA CTT TGG AAA GGA CCA GCA AAG CTC
CTC TGG AAA GGT GAA GGG GCA (TGT).

CTA AAC ACA GTG GGG GGA CAT CAA GCA III
GCC ATG CAA ATG TTA AAA GAG ACC ATC AAT GAG
GAA GCT GCA GAA TGG GAT AGA GTG CAT CCA (TGT)

Fragments from these sequences may be employed for expression of peptide fragments, conservative base changes can be made, where the modified condon(s) code for the same amino acid(s), or non-conservative changes in the coding sequence may be made, where the resulting amino acid may be a conservative or non-conservative change in the amino acid sequence, which was discussed previously.

The coding sequence may be extended at either the 5'- or 3'-terminus or both termini to extend the peptide, while retaining its epitopic site. The extension may provide for an arm for linking, e.g., to a label, such as an enzyme, for joining two or all of the peptides together in the same chain, for providing antigenic activity, or the like.

For expression, the coding sequence will be provided with start and stop condons, promoter and terminator regions and usually a replication system to provide an expression vector for expression in a cellular host, e.g., prokaryotic or eukaryotic, bacterial, yeast, mammal, etc.

The sequences by themselves, fragments thereof, or larger sequences, usually at least 15 bases, preferably at least 18 bases, may be used as probes for detection of retroviral RNA or proviral DNA. Numerous techniques are described; such as the Grunstein-Hogness technique, Southern technqiue, Northern technique, dot-blot, improvements thereon, as well as other methodology. See, for example, WO 83/02277 and Berent et al., *Biotechniques* (1985) 3:208.

Conveniently, the polypeptides may be prepared as fused proteins, where the polypeptide may be the N- or C-terminus of the fused polypeptide. The rseulting fused protein could be used directly by itself as the reagent or the subject polypeptide may be cleaved form all or a portion of the remaining sequence of the fused protein. With a polypeptide where there are no internal methionines, by introducing a methionine at the fusion site, the polypeptide may be cleaved employing cyanogen bromide. Where there is an internal methionine, it would be necessary to provide for a proteolytic cleavage site, e.g., poly-lysine and/or -arginine or combinations thereof, or the internal methionine could be substituted by an amino acid such as leucine and an N-terminal methionine added for cyanogen bromide cleavage. A wide variety of proteases, including dipeptidases, are well known, and the appropriate processing signal could be introduced at the proper site. The processing signal may have tandem repeats so as to insure cleavage, since the presence of one or more extraneous amino acids will not interfere with the utility of the subject polypeptides.

Depending upon the nature of the assay, the physiological sample, e.g., saliva, blood, plasma, or serum, may be pretreated by dilution into an assay medium, which will usually be an aqueous buffered medium employing one of a variety of buffers, such as phosphate, tris, or the like. A preferred diluent is blotto (2.5% m/v nonfat dry milk, 0.01% thimerosol, 0.005% Antifoam A in 0.01M sodium phosphate, pH 7.2, and 0.15M NaCl). Usually the pH will be in the range of about 6 to 9. The sample will then be combined with the reagent in accordance with the appropriate protocol and sufficient time allowed for binding. Where a heterogeneous system is used, usually the bindign stages will be followed by washes to minimize non-specific binding. At the end of the procedure, the label will be detected in accordance with conventional methods.

Besides the use of the subject peptides and their analogs in assays, the subject peptides may also find use by themselves or in combination in vaccines. The peptides may be formulated in a convenient manner, generally at concentrations in the range of 1 μg to 20 mg/kg of host. Physiologically acceptable media may be used as carriers, such as sterile water, saline, phosphate buffered saline, and the like. Adjuvants may be employed, such as aluminum hydroxide gel, or the like. Administration may be by injection, e.g., intramuscularly, peritoneally, subcutaneously, intravenously, etc. Administration may be one or a plurality of times, usually at one to four week intervals.

The following examples are offered by way of illustration and not by way of limitation.

EXPERIMENTAL

Peptides were assembled on a t-butyloxycarbonyl (BOC)-methylbenzylcysteine-phenyl-acetamidomethyl (PAM) polystyrene/divinylbenzene resin (Applied Biosystems, Inc., Foster City, Calif.). Symmetrical anhydride couplings were carried out in an Applied Biosystems 430A synthesizer. Benzyl-based side chain protection and BOC alpha-amine protection were used. Tryptophan was protected by the formyl moiety and methionine by its sulfoxide, both protecting groups being removed by conventional procedures.

The peptides were radiolabeled by inclusion of a $^{3}H$-glycine residue within the sequence. The peptides were deprotected and cleaved from the resin by the Tam "low-high" HF protocol (Tam et al., supra). Peptides were extracted from the resin in 5% acetic acid and subjected to gel filtration chromatography in 5% acetic acid.

The peptides synthesized above were sometimes oxidized through the cysteine residues to form network polymers. This was carried out by dissolving the lyophilized peptide in 0.1M carbonate/bicarbonate, 6M guanidine-HCl pH 9.0 at a concentration of 5-10 mg/ml. The pH of the resulting solution is checked and adjusted to a pH of 9.0 if requred and the solution is allowed to stir at room temperature overnight. Resultant solutions are used as a coating antigen in the ELISA assays described below.

Analysis by ELISA

Peptides 123, 124 and 126 were stored as stock solutions of 4 mg/ml in 6M Gu-HCl or as the oxidized peptide stocks described above. Peptides 158 and 158E were stored at 4 mg/ml in 0.05M carbonate/bicarbonate buffer (pH 9.6). The peptides were diluted in 0.05M carbonate/dicarbonate buffer (pH 9.6) to a final concentration of 5-800 μg/ml. One hundred μl aliquots were added per microtiter well and incubated at 4° C. overnight. Plates were then blocked with blotto (5% [w/v] nonfat dry mil, 0.01% thimerasol, 0.01% Antifoam A in 0.01M sodium phosphate, pH 7.2, 0.15M sodium chloride) for one hour at 37° C. Serum or plasma samples were diluted 1:101 or 1:21 with diluent (2.5% [w/v] nonfat dry milk, 0.01% thimerasol, 0.005% Antifoam A in 20 mM sodium citrate) and 100 μl of diluted serum or plasma was added per well for one hour at b 37° C. The sera or plasma were aspirated, and the plates were washed three times in wash buffer (0.15M NaCl, 0.05% [w/v] Tween 20) before adding 100 μl of the goat anti-human Ig/horseradish peroxidase conjugate (diluted 1:10,000 indiluent containing 1% normal goat serum in citrate buffer, pH 7.0) for one hour at 37° C. The conjugate was removed, and the plates were again washed three times as described above. The ELISA assay was developed by adding 100 μl/well of substrate solution (80 μl/ml tetramethylbenzidine, 0.0015% hydrogen peroxide in citrate/phosphate buffer pH 5.0) for thirty minutes at room temperature. Reactions were stopped with the addition of 100 μl of 3N $H_2SO_4$ per well, and the ratio of the optical density at 450 nm to 630 nm was determined by an atuomated ELISA reader.

Peptides from the pol region were tested in the ELISA format replacing whole virus lysate in the Genetic Systems Corp. LAV EIA assay. Sera were diluted 1:101 and the peptides were used in both oxidized and unoxidized forms. Peptide I(123) recognized 30 of 34 positive test sera as positive and 11 of 11 negative sera as negative (Table I). Peptide II recognized 32 of 34 positive sera as positive and 11 of 11 negative sera as negative. The removal of 12 amino acids from the amion terminus of peptide II did not reduce the ability of the sequence to differentiate HIV positive sera.

Use of the peptides in an oxidized form, which is not necessary for these particular peptides to function in the assay, increased the total amount of signal from each sample. This may be due to an increase in the amount of peptide adsorbed to the microtiter plate.

Peptide III(158) from the gag region of the HIV genome tested in the ELISA format was used, plating 80 μg/well, toscreen both plasma and serum samples. The data summarized in Table II demonstrates that paptide 158 recognizes 13 of 17 p25 positive plasma and sera.

In an alternate assay peptide 158E, a modification of peptide 158 in which the methionines were replaced with norleucine, the sera or plasma were diluted 1:21 in diluent buffer, the incubation times with the sample and conjugate were reduced to 30 min, and the washes between the steps were increased to six. These changes resulted in 17 of 17 positive samples being recognized.

Results of the serum screen are presented in Table I and are summarized as follows:

TABLE 1

ELISA Data for Serum Screen of pol Peptides

| Serum I.D. Number | Diagnosis | Western Blot Confirmation | ELISA Using Whole Virus Lysate | 123 Peptide 0.5 μg/well | 123ox Peptide 0.5 μg/well | 124 Peptide 0.25 μg/well | 124ox Peptide 0.25 μg/well | 126 Peptide 1.0 μg/well | 126ox Peptide 2.0 μg/well |
|---|---|---|---|---|---|---|---|---|---|
| 1 | ARC[1] | Pos. | 2.079 | 1.439 | 1.874 | 1.617 | 1.232 | 0.978 | 1.489 |
| 2 | ARC | Pos. | 1.995 | 0.632 | 0.435 | 0.324 | 0.289 | 0.436 | 0.692 |
| 3 | ARC | Pos. | 1.803 | 1.334 | 1.407 | 0.965 | 0.497 | 0.783 | 1.245 |
| 4 | HHM[2] | Pos. | 1.771 | 1.864 | 2.199 | 2.229 | 2.066 | 0.368 | 0.633 |

TABLE 1-continued

| Serum I.D. Number | Diagnosis | Western Blot Confirmation | ELISA Data for Serum Screen of pol Peptides: ELISA Using Whole Virus Lysate | 123 Peptide 0.5 μg/well | 123ox Peptide 0.5 μg/well | 124 Peptide 0.25 μg/well | 124ox Peptide 0.25 μg/well | 126 Peptide 1.0 μg/well | 126ox Peptide 2.0 μg/well |
|---|---|---|---|---|---|---|---|---|---|
| 5 | LAS[3] | Pos. | 2.158 | 1.819 | 2.019 | 1.765 | 1.506 | 0.781 | 1.111 |
| 6 | LAS | Pos. | 2.217 | 1.899 | 2.181 | 2.016 | 1.770 | 0.667 | 1.058 |
| 7 | ARC | Pos. | 1.836 | 0.378 | 0.480 | 0.179 | 0.150 | 0.761 | 1.304 |
| 8 | HHM | Pos. | 2.147 | 1.112 | 1.217 | 0.833 | 0.618 | 0.317 | 0.581 |
| 9 | LAS | Pos. | 2.333 | 1.711 | 2.384 | 2.397 | 2.394 | 0.995 | 1.689 |
| 11 | AIDS[4] | Pos. | 1.576 | 0.767 | 0.856 | 0.365 | 0.352 | 0.825 | 1.084 |
| 12 | HHM | Neg. | 0.115 | 0.220 | 0.250 | 0.124 | 0.164 | 0.099 | 0.201 |
| 13 | LAS | Pos. | 1.970 | 1.677 | 2.021 | 2.063 | 1.720 | 0.636 | 1.053 |
| 14 | LAS | Pos. | 2.398 | 1.986 | 2.335 | 2.381 | 2.283 | 1.293 | 1.932 |
| 15 | LAS | Pos. | 1.972 | 0.440 | 0.518 | 0.260 | 0.269 | 0.457 | 0.944 |
| 16 | AIDS | Pos. | 1.751 | 0.756 | 0.904 | 0.529 | 0.410 | 0.625 | 0.916 |
| 17 | LAS | Pos. | 2.487 | 1.630 | 2.283 | 2.309 | 2.161 | 1.155 | 1.859 |
| 18 | LAS | Pos. | 2.258 | 1.252 | 1.448 | 0.886 | 0.732 | 0.750 | 1.258 |
| 19 | LAS | Pos. | 1.777 | 1.437 | 1.759 | 1.509 | 1.151 | 0.250 | 0.628 |
| 20 | HHM | Neg. | 0.128 | 0.284 | 0.306 | 0.154 | 0.175 | 0.205 | 0.247 |
| 21 | LAS | Pos. | 2.026 | 1.625 | 1.948 | 1.517 | 1.097 | 1.155 | 1.606 |
| 22 | LAS | Pos. | 2.511 | 0.812 | 0.939 | 0.334 | 0.280 | 1.157 | 1.760 |
| 23 | ARC | Pos. | 2.125 | 1.744 | 2.275 | 2.201 | 2.110 | 0.923 | 1.089 |
| 24 | LAS | Pos. | 2.179 | 1.571 | 2.292 | 2.020 | 1.849 | 0.718 | 1.226 |
| 25 | LAS | Pos. | 1.884 | 0.937 | 1.245 | 0.717 | 0.553 | 0.363 | 0.762 |
| 26 | LAS | Pos. | 2.101 | 1.705 | 2.456 | 2.431 | 2.369 | 0.517 | 0.898 |
| 27 | LAS | Pos. | 2.053 | 1.066 | 1.304 | 0.316 | 0.279 | 1.269 | 1.837 |
| 28 | LAS | Pos. | 2.106 | 1.062 | 1.324 | 0.759 | 0.575 | 0.653 | 0.997 |
| 29 | LAS | Pos. | 2.328 | 1.926 | 2.381 | 2.430 | 2.392 | 1.258 | 1.741 |
| 30 | AIDS | Pos. | 1.821 | 0.731 | 0.683 | 0.413 | 0.360 | 0.470 | 0.877 |
| 31 | LAS | Pos. | 2.363 | 2.105 | 2.446 | 2.446 | 2.416 | 0.942 | 1.535 |
| 32 | HHM | Neg. | 0.121 | 0.306 | 0.328 | 0.148 | ND | 0.187 | 0.272 |
| 33 | HHM | Neg. | 0.104 | 0.366 | 0.387 | 0.163 | ND | 0.127 | 0.283 |
| 34 | LAS | Pos. | 1.947 | 1.665 | 1.979 | 2.149 | ND | 1.923 | 2.472 |
| 35 | LAS | Pos. | 1.710 | 0.737 | 0.667 | 0.469 | ND | 0.223 | 0.399 |
| 36 | HHM | Pos. | 2.091 | 0.844 | 0.991 | 0.586 | 0.616 | 0.283 | 0.523 |
| 37 | ARC | Pos. | 1.193 | 0.359 | 0.429 | 0.195 | 0.250 | 0.169 | 0.454 |
| 38 | ARC | Pos. | 1.357 | 1.188 | 1.577 | 1.063 | 0.979 | 0.393 | 0.840 |
| 41 | ? | Pos. | 0.918 | 0.463 | 0.421 | 0.214 | 0.299 | 0.129 | 0.189 |
| 16* | Donor | Neg. | 0.079 | 0.265 | 0.264 | 0.116 | 0.186 | 0.099 | 0.200 |
| 21* | Donor | Neg. | 0.129 | 0.300 | 0.297 | 0.148 | 0.235 | 0.110 | 0.243 |
| 48* | Donor | Neg. | 0.100 | 0.267 | 0.283 | 0.119 | 0.231 | 0.102 | 0.268 |
| 32* | Donor | Neg. | 0.078 | 0.296 | 0.377 | 0.121 | 0.289 | 0.099 | 0.246 |
| 31* | Donor | Neg. | 0.181 | 0.309 | 0.302 | 0.126 | 0.237 | 0.192 | 0.294 |
| 50* | Donor | Neg. | 0.077 | 0.254 | 0.331 | 0.157 | 0.243 | 0.241 | 0.408 |
| 52* | Donor | Neg. | 0.085 | ND[5] | 0.263 | 0.117 | 0.229 | ND | 0.263 |
| TRIMAR | Pool | Pos. | 2.459 | 2.001 | 2.298 | 2.049 | 1.816 | 0.938 | 1.307 |

[1]ARC = AIDS-Related Complex
[2]HHM = Healthy Homosexual Males
[3]LAS = Lymphadenopathy Syndrome
[4]AIDS = Acquired Immune Deficiency Syndrome
[5]ND = Not Determined

TABLE 2

| Sample I.D. Number | ELISA Results for Plasma and Serum Samples with Peptide 158 and 158E as Antigen: Western Blot Confirmation of P25 | ELISA Using Whole Virus Lysate | Peptide 158 (1:101) | Peptide 158E (1:21) |
|---|---|---|---|---|
| A | Pos. | 2.088 | 0.784 | 2.034 |
| B | Neg. | 0.108 | 0.151 | 0.110 |
| C | Pos. | 0.271 | 0.095 | 0.725 |
| D | Pos. | ND | ND | 1.448 |
| E | Neg. | 0.107 | 0.072 | 0.182 |
| F | Neg. | 0.102 | 0.146 | 0.366 |
| G | Pos. | 1.998 | 1.905 | 2.563 |
| H | Pos. | 2.074 | 1.441 | 2.393 |
| I | Pos. | 1.944 | 1.980 | 2.536 |
| J | Pos. | 1.245 | 0.845 | 1.907 |
| K | Pos. | 2.046 | 2.235 | 2.460 |
| L | Pos. | 0.948 | 0.374 | 2.121 |
| M | Pos. | 2.092 | 1.395 | 2.368 |
| N | Pos. | 2.153 | 2.043 | 1.757 |
| O | Pos. | 2.068 | 1.387 | 2.479 |
| P | Pos. | 0.702 | 0.120 | 1.617 |
| Q | Pos. | 1.267 | 0.099 | 1.824 |
| R | Pos. | 2.147 | 1.908 | 2.219 |
| S | Pos. | 1.393 | 0.267 | 2.306 |
| T | Pos. | 1.189 | 0.724 | 2.245 |
| N32 | Neg. | 0.334 | 0.100 | ND |

TABLE 2-continued

| Sample I.D. Number | ELISA Results for Plasma and Serum Samples with Peptide 158 and 158E as Antigen: Western Blot Confirmation of P25 | ELISA Using Whole Virus Lysate | Peptide 158 (1:101) | Peptide 158E (1:21) |
|---|---|---|---|---|
| N31 | Neg. | 0.107 | 0.090 | ND |
| 10806 | ND | 0.051 | ND | 0.257 |
| 10807 | ND | 0.065 | ND | 0.275 |

It is evident from the foregoing results that by employing one or a combination of peptides of the subject invention, a sensitive, accurate test for the presence of antibodies to AIDS is provided. The subject peptides can be used by themselves or in combination with a screening assay or confirmatory assay, whereas the complete lysate or complete antigens may be employed as an independent procedure. Furthermore, because of the specificties of the peptides, one would anticipate that the DNA sequences coding for the peptides would also find similar specificty in a DNA hybridization assay. Thus, the subject invention allows for the detection of patients who have been exposed to the retroviral etiologic agent of lymphadenopathy syndrome and/or AIDS.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The ivnention now being fully described, it will be apparent to one of ordinary skill in the art that many changes and modifications can be made thereto without departing from the spirit or scope of the appended claims.

What is claimed is:

1. In a method for detecting the presence of antibody to HIV virus where a sample is combined with a composition having epitopic sites immunologically competitive with HIV epitopic sites, whereby antibodies bind to each such protein composition to form at least one specific binding pair complex and the amount of complex formation is determined, the improvement which comprises:

combining with said sample a composition comprising a reagent containing at least one peptide which has at least six contiguous amino acids and fewer than fifty amino acids in a sequence which comes within the sequence of at least one of the following peptide sequences:

Y-Gln-Val-Arg-Asp-Gln-Ala-Glu-His-Leu-Lys-Thr-Ala-Val-Gln-Met-Ala-Val-Phe-Ile-His-Asn-Phe-Lys-Arg-Lys-Gly-Gly-Ile-Gly-Gly-Tyr-Ser-Ala-Gly-Glu-Arg-Ile-Val-Asp-Ile-Ile-Ala-Thr-Asp-Ile-X-Z;

Y-Ile-Ala-Thr-Asp-Ile-Gln-Thr-Lys-Glu-Leu-Gln-Lys-Gln-Ile-Thr-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z; or

Y-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z;

wherein Z is OH or $NH_2$, and X and Y, if present, are amino acids added to facilitate covalent coupling, wherein amino acids in the sequence may be inserted, deleted and substituted so long as immunoreactivity to antibodies to HIV is retained, and wherein each of said peptides is present as a free peptide or is conjugated to a soluble macromolecular carrier for which antibodies are unlikely to be encountered in human sera.

2. A method according to claim 1, wherein oen of the peptides has one of the following sequences:

Y-Gln-Val-Arg-Asp-Gln-Ala-Glu-His-Leu-Lys-Thr-Ala-Val-Gln-Met-Ala-Val-Phe-Ile-His-Asn-Phe-Lys-Arg-Lys-Gly-Gly-Ile-Gly-Gly-Tyr-Ser-Ala-Gly-Glu-Arg-Ile-Val-Asp-Ile-Ile-Ala-Thr-Asp-Ile-X-Z;

Y-Ile-Ala-Thr-Asp-Ile-Gln-Thr-Lys-Glu-Leu-Gln-Lys-Gln-Ile-Thr-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z; or

Y-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z;

3. A method according to claim 1, wherein said composition is bound to a solid surface.

4. The method of claim 1 wherein X is Cys, Y is Cys-Gly-Gly-Cys-, and Z is $NH_2$.

5. A method for determining the presence of antibodies to HIV in a physiological fluid, said method comprising:

introducing a sample of physiological fluid into a sample container coated at least in part with at elast one peptide having at elast six contiguous amino acids and fewer than fifty amino acids which comes within the sequence of at least one of the following peptide sequences:

Y-Gln-Val-Arg-Asp-Gln-Ala-Glu-His-Leu-Lys-Thr-Ala-Val-Gln-Met-Ala-Val-Phe-Ile-His-Asn-Phe-Lys-Arg-Lys-Gly-Gly-Ile-Gly-Gly-Tyr-Ser-Ala-Gly-Glu-Arg-Ile-Val-Asp-Ile-Ile-Ala-Thr-Asp-Ile-X-Z;

Y-Ile-Ala-Thr-Asp-Ile-Gln-Thr-Lys-Glu-Leu-Gln-Lys-Gln-Ile-Thr-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z; or

Y-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z;

wherein Z is OH or $NH_2$, and X and Y, if present, are amino acids added to facilitate covalent coupling, wherein amino acids in the sequence may be inserted, deleted and substituted so long as immunoreactivity to antibodies to HIV is retained, and wherein each of said peptides is present as a free peptide or is conjugated to a soluble macromolecular carrier for which antibodies are unlikely to be encountered in human sera;

incubating for a sufficient time for complex formation to occur between said peptide and said antibodies to HIV; and determining the formation of complex by employing a labeled specific binding protein which binds to said complex and provides a detectable signal.

6. A method acocrding ot claim 5, wherein said peptide is conjugated to a water soluble protein of at least 5 kDal as said macromolecule.

7. A method according ot claim 5, wherein two of said peptides are covalently linked together through a bond or bridging group.

8. A method according to claim 5, wherein said specific binding protein is antibody to human immunoglobulin.

9. The method of claim 5 wherein X is Cys, Y is Cys-Gly-Gly-Cys-, and Z is $NH_2$.

10. A method for determining the presence of antibodies to HIV in a physiological fluid, said method comprising;

combining a human serum, plasma or blood sample with at least one labeled peptide having at least six contiguous amino acids and fewer than fifty amino acids in a sequence which comes within the sequence of at least one of the followign peptide sequences:

Y-Gln-Val-Arg-Asp-Gln-Ala-Glu-His-Leu-Lys-Thr-Ala-Val-Gln-Met-Ala-Val-Phe-Ile-His-Asn-Phe-Lys-Arg-Lys-Gly-Gly-Ile-Gly-Gly-Tyr-Ser-Ala-Gly-Glu-Arg-Ile-Val-Asp-Ile-Ile-Ala-Thr-Asp-Ile-X-Z;

Y-Ile-Ala-Thr-Asp-Ile-Gln-Thr-Lys-Glu-Leu-Gln-Lys-Gln-Ile-Thr-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z; or

Y-Lys-Ile-Gln-Asn-Phe-Arg-Val-Tyr-Tyr-Arg-Asp-Ser-Arg-Asp-Pro-Leu-Trp-Lys-Gly-Pro-Ala-Lys-Leu-Leu-Trp-Lys-Gly-Glu-Gly-Ala-X-Z;

wherein Z is OH or $NH_2$, and X and Y, if present, are amino acids added to facilitate covalent coupling, wherein amino acids in the sequence may be inserted, deleted and substituted so long as immunoreactivity to antibodies to HIV is retained, and wherein each of said peptides is present as a free peptide or is conjugated to a soluble macromolecular carrier for which antibodies are unlikely to be encountered in human sera;

incubating for a sufficient time for complex formation to occur between said labeled peptide and said antibodies to HIV; and determining the formation of complex as a result of change in a detectable signal resulting from complex formation.

11. A method according ot claim 10, wherein said label is a fluorescer.

12. A method according to claim 11, wherein complex formation is determined by fluorescence polarization.

13. A method according to claim 10, wherein said label is an enzyme.

14. A method according to claim 13, wherein complex formation is determined as a result of enzyme activity modulation.

15. A peptide composition, immunoreactive to antibodies to HIV, having from six contiguous amino acids to about fifty amino acids, whereins aid peptide includes amino acids from within the following sequence:

(I) (126)

Y—Gln—Val--Arg—Asp—Gln—Ala—Glu—His—Leu—Lys—Thr—Ala—Val—Gln—Met—Ala—Val—Phe—Ile—His—Asn—Phe—Lys—Arg—Lys—Gly—Gly—Ile—Gly—Gly—Tyr—Ser—Ala—Gly—Glu—Arg—Ile—Val—Asp—Ile—Ile—Ala—Thr—Asp—Ile—X—Z;

(II) (123)

-continued

Y—Ile—Ala—Thr—Asp—Ile—Gln—Thr—Lys—Glu—Leu—Gln—Lys—Gln—Ile—Thr—Lys—Ile—Gln—Asn—Phe—Arg—Val—Tyr—Tyr—Arg—Asp—Ser—Arg—Asp—Pro—Leu—Trp—Lys—Gly—Pro—Ala—Lys—Leu—Leu—Trp—Lys—Gly—Glu—Gly—Ala—X—Z; or (IIa) (124)

Y—Lys—Ile—Gln—Asn—Phe—Arg—Val—Tyr—Tyr—Arg—Asp—Ser—Arg—Asp—Pro—Leu—Trp—Lys—Gly—Pro—Ala—Lys—Leu—Leu—Trp—Lys—Gly—Glu—Gly—Ala—X—Z.

wherein Z is OH or $NH_2$, and X and Y, if present, are amino acids added to facilitate covalent coupling, wherein amino acids in the sequence may be inserted, deleted and substituted so long as immunoreactivity to antibodies to HIV is retained, and wherein each of said peptides is present as a free peptide or is conjugated to a soluble macromolecular carrier for which antibodies are unlikely to be encountered in human sera.

16. The peptide composition of claim 15, wherein X and Y independently represent one or more Cys or a combination of one or more Cys with one or more linker amino acids.

17. The peptide composition of claim 16, wherein X and Y together represent at least three Cys residues.

18. The peptide composition of claim 15, wherein at least one of X or Y represents two Cys residues separated by one or more α-amino acid residues having a single side chain containing no more than four carbon atoms.

19. The peptide composition of claim 18, wherein said α-amino acid residues are 1-3 glycine residues.

20. The peptide composition of claim 15, wherein said protein has formula (I) (126).

21. The peptide composition of claim 15, wherein said protein has formula (II) (123).

22. The peptide composition of claim 15, wherein said protein has formula (IIa) (124).

23. The peptide of claim 15 wherein X is Cys, Y is Cys-Gly-Gly-Cys-, and Z is $NH_2$.

* * * * *